United States Patent [19]
Alvarez

[11] Patent Number: 5,935,800
[45] Date of Patent: *Aug. 10, 1999

[54] ASSAYS AND KITS FOR DETERMINING MALE FERTILITY

[75] Inventor: Juan G. Alvarez, Boston, Mass.

[73] Assignee: Beth Israel Deaconess Medical Center, Boston, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/719,756

[22] Filed: Sep. 25, 1996

Related U.S. Application Data

[63] Continuation-in-part of application No. 08/550,664, Oct. 31, 1996, which is a continuation-in-part of application No. 08/332,825, Oct. 31, 1995, which is a continuation-in-part of application No. 08/332,826, Oct. 31, 1994, abandoned.

[51] Int. Cl.[6] .......................... G01N 33/52; G01N 33/53; G01N 21/00
[52] U.S. Cl. ................. 435/7.8; 422/55; 422/61; 422/68.1; 422/101; 435/2; 435/7.21; 435/288.7; 435/806; 435/975; 435/40.5; 436/503; 436/518; 436/63; 436/86; 436/164; 436/178; 436/808; 436/810; 436/906
[58] Field of Search .................................. 435/7.21, 2, 6, 435/7.4, 7.8, 287.2, 288.3, 806, 971, 975, 288.4, 40.5; 436/503, 518, 63, 86, 164, 178, 906, 808, 810; 422/55, 61, 68.1, 101

[56] References Cited

U.S. PATENT DOCUMENTS

| | | |
|---|---|---|
| 3,909,363 | 9/1975 | Bucalo . |
| 4,007,087 | 2/1977 | Ericsson ................................. 195/1.8 |
| 4,009,260 | 2/1977 | Ericsson ................................. 424/105 |
| 4,185,085 | 1/1980 | Cartensen .................................. 435/2 |
| 4,559,309 | 12/1985 | Evenson et al. ........................... 436/63 |
| 4,683,213 | 7/1987 | Ax ............................................. 436/63 |
| 4,804,537 | 2/1989 | Bergman et al. ........................ 424/105 |
| 4,880,732 | 11/1989 | Resli et al. ............................... 435/29 |
| 4,945,044 | 7/1990 | Huszar ..................................... 435/17 |
| 5,028,526 | 7/1991 | Deutsch ................................. 435/7.21 |
| 5,055,411 | 10/1991 | Ericcson et al. .......................... 436/63 |
| 5,068,089 | 11/1991 | Ericsson et al. .......................... 422/61 |
| 5,185,246 | 2/1993 | Deutsch ................................. 435/7.21 |
| 5,219,729 | 6/1993 | Hodgen ................................. 435/7.21 |
| 5,429,746 | 7/1995 | Shadle et al. ........................... 210/635 |
| 5,434,057 | 7/1995 | Dorian ..................................... 435/18 |

FOREIGN PATENT DOCUMENTS

| | | |
|---|---|---|
| WO 87/02382 | 4/1987 | WIPO . |
| WO 96/13225 | 5/1996 | WIPO . |

OTHER PUBLICATIONS

R.J. Aitken et al., "Relationship Between Iron–Catalyzed Lipid Peroxidation Potential and Human Sperm Function", *Chemical Abstracts,* vol. 119, No. 11, abstracts No. 114355, 644 (1993).

R.J. Aitken et al., "Relationship Between Iron–Catalyzed Lipid Peroxidation Potential and Human Sperm Function", *J. Reprod. Fertil.,* 98(1), 257–65 (1993).

John Aitken and Helen Fisher, "Reactive Oxygen Species Generation and Human Spermatozoa: The Balance of Benefit and Risk" *BioEssays,* vol. 16, No. 4, pp. 259–267 (Apr. 1994).

R. John Aitken, Janes S. Clarkson and Simon Fishel, "Generation of Reactive Oxygen Species, Lipid Peroxidation, and Human Sperm Function", *Biology of Reproduction,* vol. 40, 183–197 (1989).

(List continued on next page.)

*Primary Examiner*—James C. Housel
*Assistant Examiner*—James L. Grun
*Attorney, Agent, or Firm*—Lahive & Cockfield, LLP

[57] ABSTRACT

Assays and kits for identifying fertile sperm samples (e.g. for use in an assisted reproductive technology or as an indication of an ineffective male contraception (vasectomy)) and sub-fertile sperm samples (e.g. as an indication of a potentially infertile male donor or an effective male contraception) are disclosed.

16 Claims, 8 Drawing Sheets

OTHER PUBLICATIONS

J.G. Alvarez, D. Minaretzis, J.F. Mortola and I.E. Thompson, Dept. of Ob&Gyn/Boston IVF, Beth Israel Hospital, Harvard Medical School, Boston, MA, Sperm Stress Test: A Novel Test that Predicts Pregnancy Outcome in Assisted Reproductive Technologies (Art),. Abstract Form from *The American Fertility Society 50th Annual Meeting,* Nov. 5–10, 1994 (mailed Oct. 5, 1994).

J.G. Alvarez, M.M. Alper, S.P. Oskowitz, E. Sullivan and J. Mortola, Dept. of Ob&Gyn/Boston IVF, Beth Israel Hospital, Harvard Medical School, Boston, MA (Spon: B. Sachs), "Superoxide Dismutase Activity in Human Sperm Correlates with Pregnancy Rate after In Vitro Fertilization", Scientific Abstracts, 246 (mailed in Mar. 1994).

Juan G. Alvarez and Bayard T. Storey, "Evidence for Increased Lipid Peroxidative Damage and Loss of Superoxide Dimutase Activity as a Mode of Sublethal Cryodamage to Human Sperm During Cryopreservation", *Journal of Andrology,* vol. 13, No. 3, pp. 232–241 (May/Jun. 1992).

Juan G. Alvarez and Bayard T. Storey, "Evidence that Membranes Stress Contributes More than Lipid Peroxidation to Sublethal Cryodamage in Cryopreserved Human Sperm: Glycerol and other Polyols as Sole Cryoprotectant", *Journal of Andrology,* vol. 14, No. 3, pp. 199–209 (May/Jun. 1993).

Crabbe, M.J.C. "The Development of A Qualitative Assay For Male Infertility From A Study of Enzymes in Human Semen", *Chemical Abstracts,* vol. 87, No. 25, abstract no. 198648, 493 (1977).

Juan G. ALvarez, Jaime L. Lasso, Luis Blasco, Rocio C. Nunez, Susan Heyner, Pedro P. Caballero and Bayard T. Storey, "Centrifugation of Human Spermatozoa Induces Sublethal Damage; Separation of Human Spermatozoa from Seminal Plasma by a Dextran Swim–up Procedure without Centriguation Extends their Motile Lifetime", *Human Reproduction,* vol. 8, No. 7, pp. 1087–1092 (1993).

Juan G. Alvarez, Joseph C. Touchstone, Luis Blasco and Bayard T. Storey, "Spontaneous Lipid Peroxidation and Production of Hydrogen Peroxide and Superoxide in Human Spermatozoa–Superoxide Dismutase as Major Enzyme Protectant Against Oxygen Toxicity", *Journal of Andrology,* vol. 8, No. 5, pp. 338–348, (Sep./Oct. 1987).

Crabbe, M.J.C. "The Development of A Qualitative Assay For Male Infertility From A Study of Enzymes in Human Semen", *J. Reprod. Fertil.,* 51(1), 73–6 (1977).

Cesar G. Fraga, Paul A. Motchnik, Mark K. Shigenaga, Harold J. Helbock, Robert A. Jacob, and Bruce N. Ames, "Ascorbic Acid Protects Against Endogenous Oxidative DNA Damage in Human Sperm", *Proc. Natl. Acad. Sci. USA,* vol. 88, pp. 11003–11006, (Dec. 1991).

Huszar, G. and Vigue, L., "Correlation Between the Rate of Lipid Peroxidation and Cellular Maturity as Measured by Creatine Kinase Activity in Human Spermatozoa", *Journal of Andrology,* vol. 15, No. 1, pp. 71–77 (Jan./Feb. 1994).

Schill, W.B., "Indications For Determination of Acrosin Activity", *Andrologia,* 18(5), 548–52 (1986), Abstract only.

Schill, W.B., "Indications For Determination of Acrosin Activity", *Chemical Abstracts,* vol. 106, No. 3, abstract No.16572, 431 (1987).

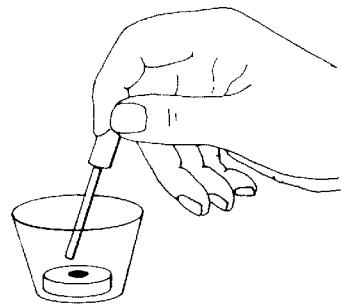
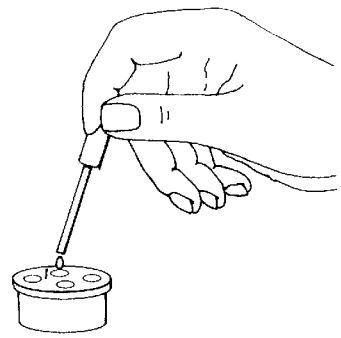
FIG. 1A  FIG. 1B
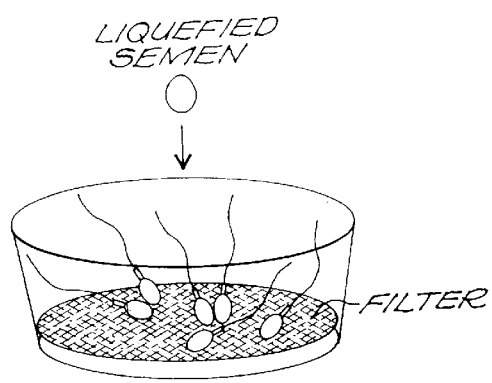
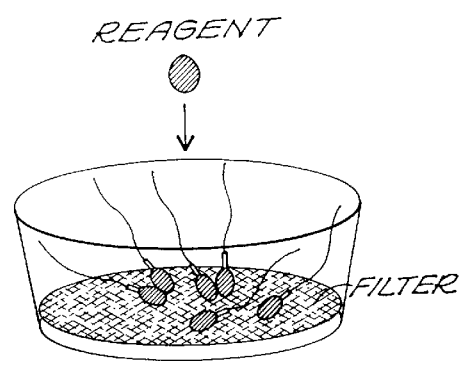
FIG. 1C  FIG. 1D
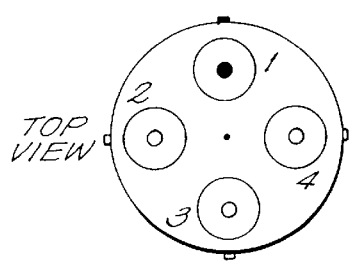
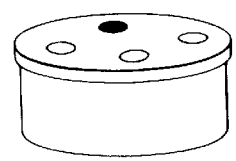
FIG. 1E  FIG. 1F 1. ADD ONE DROP OF WASHED SPERM TO A TEST TUBE CONTAINING PROTEIN A BOUND TO GOLD PARTICLES

2. WAIT 15 MINUTES

15 MINUTES

3. ADD ONE DROP OF WASHED SPERM/ANTIBODY MIXTURE TO WELL #1 OF FILTER MODULE AND ALLOW TO DRAIN

4. ADD ONE DROP OF DISTILLED WATER

DISTILLED WATER

5. COMPARE TO COLOR CHART

ASSAYS AND KITS FOR DETERMINING MALE FERTILITY

RELATED APPLICATION

This application is a continuation-in-part application of U.S. Ser. No. 08/550,664 filed on Oct. 31, 1996, which itself is a continuation-in-part application of U.S. Ser. No. 08/332,825 filed on Oct. 31, 1995, now allowed, which is a CIP U.S. Ser. No. 08/332,826 filed on Oct. 31, 1994, now abandoned, the contents of all prior applications are expressly incorporated herein by reference.

BACKGROUND OF THE INVENTION

Determining Male Fertility

According to recent studies, male infertility (e.g. defective spermatogenesis or testicular obstruction) is responsible almost 40% of the time that a couple is unable to conceive a child. In addition, use of male contraceptives is on the rise. According to current estimates, more than 500,000 vasectomies are performed in the U.S. each year and about 10,000,000 are performed worldwide. In addition to vasectomies, a variety of oral contraceptives for use by males are in development. Although male contraceptives decrease the probability that a fertile male will initiate a pregnancy, no male contraceptive is 100% effective. Further, most male contraceptives require a certain period of time in which to take effect.

For a semen sample to be considered fertile according to standards set by the World Health Organization (WHO), at least two 1.5–5.0 milliliter ejaculate volumes obtained from a male must contain a sperm density of greater than 20 million spermatozoa/mL and/or a percent motility of 60% with a forward progression greater than 2 (on a 1–4 scale). In addition, the semen samples should show no evidence of sperm agglutination, leukocytospermia (pyospermia) or hyperviscosity (Sigman, M., et al., Evaluation of the non-fertile male. In: Lipschultz, L I and S S Howards eds. *Infertility in the Male*, 2nd ed. Chicago: Mosby-Year Book, 1991; p.184). A leukocyte count in semen that is greater than 1 million/ml is diagnostic by WHO criteria of leukocytospermia, a condition that is frequently associated with genitourinary infection, antisperm antibodies and male infertility.

By convention, male infertility is diagnosed based on low sperm motility and/or count. However, motility analyses can produce false negatives, since fertile sperm may appear non-motile due to damage sustained during processing. With regard to sperm count, 20 million spermatozoa/mL or greater is generally considered to be in the fertile range. However, non-motile, non-fertile sperm can be included in the count. Sperm count and motility are typically assessed using commercially available instruments, such as light microscopes and computerized videoanalysis systems.

U.S. Pat. No. 5,068,089 describes a home kit for testing fertility of human sperm based on ability of the sperm to reduce a dye. The extent of reduction (displayed calorimetrically), is said to be indicative of sperm fertilizing ability. However, this test is time consuming, requires incubation at a temperature above room temperature and does not distinguish between reduction due to sperm cells or other cells, which may be present in a semen sample.

U.S. Pat. No. 5,219,729 describes a laboratory assay for determining the fertilizing ability of sperm based on the affinity of binding to an oocyte zona pellucida fragment. The tighter the binding, the greater the fertilizing ability of the sperm sample. However, this assay requires freshly prepared oocyte fragments and at least four hour's time during which the sperm must be kept in contact with the oocyte fragment.

U.S. Pat. No. 5,434,057 describes assays and kits for determining male fertility based on the detection of fumarase activity. However, since fumarase is ubiquitously present in cells including cells that may be present in a sperm sample (epithelial, leukocyte and bacterial or fungal), whether fumarase activity is an accurate indicator of sperm count and motility, as claimed in the patent, is dubious.

A simple, rapid and accurate assay for determining the fertility of a sperm sample in a reference laboratory, doctor's office or at home is needed.

Assisted Reproductive Technologies

Assisted reproductive technologies (ARTs), such as in vitro fertilization (IVF), gamete intrafallopian transfer (GIFT), intrauterine insemination (IUI) and sperm intracytoplasmic injection (ICSI) offer ways to initiate a pregnancy when natural approaches have been unsuccessful. These techniques are also useful for breeding animals or producing transgenic animals.

However, ARTs do not always result in a successful pregnancy. For example, IVF has an estimated success rate of about 25%, while GIFT is estimated as being successful in about 31% of attempts. One factor, which may contribute to an unsuccessful ART attempt is that not all sperm samples are capable of fertilization. According to recent studies, male infertility is responsible almost 40% of the time that a couple is unable to conceive a child.

In addition, the chance that a sperm sample will be incapable of initiating a pregnancy is increased when that sample has been stored for any period of time or cryopreserved. This finding has particular significance, since cryopreserved sperm is typically used in ARTs. Cryopreservation can result in sublethal cryodamage, in which cell fertility post-thaw is lost more rapidly at later times than in fresh cells. Sublethal cryodamage has been shown to be due in part to membrane embrittlement during the phase transitions involved in freezing and thawing (Alvarez, J. G. and B. T. Storey (1993) *J. Androl*. 14(3): 199–209). To a lesser degree, sublethal cryodamage has been shown to be caused by spontaneous lipid peroxidation (SLP) of sperm phospholipids (Alvarez, J. G. and B. T. Storey (1993) *J Androl*. 14(3): 199–209 and J. G. Alvarez and B. T. Storey (1992) *J. Androl* 13(3): 232–241). Spontaneous lipid peroxidation appears to be the major factor limiting the motile lifetime of sperm that has not been cryopreserved (Alvarez, J. G. and B. T. Storey (1988) Gamet Res. 23:77–90; and Alvarez, J. G. and B. T. Storey (1985) Biol. Reprod. 32: 342–351). The selective oxidation of phospholipid-bound polyunsaturated fatty acid moieties resulting from spontaneous lipid peroxidation leads to extensive oxidative damage to the sperm plasma and acrosomal membranes and DNA.

However, cryopreservation of sperm samples is routinely performed in ART procedures and in fact is required in order to test the donor for the presence of transmissible infectious agents (e.g., HIV) prior to insemination. For example, a donor is typically tested six months after producing a particular sample and only if the test is negative will the stored sample be used for insemination.

More and more couples are turning to ARTs to conceive a child. In addition, ARTs are increasingly being used by breeders of livestock and in generating transgenic animals. Methods for identifying only fertile sperm samples for use in an ART would increase their success rate.

SUMMARY OF THE INVENTION

In general, the invention features novel assays and kits for determining male fertility based on analyzing a sperm sample. Certain of the assays can be performed by most anyone and have been prepared as kits for home use. Other of the assays require more skill to perform and/or require special equipment for analysis and therefore have been prepared as kits for performance in a laboratory (e.g. andrology lab) or at a doctor's office.

In preferred embodiments, the fertility assays are based on detecting the intensity of certain colored sperm reagents as an indication of the concentration of sperm in the sample (e.g. semen or washed sperm). In particularly preferred assays for identifying fertile sperm samples, the presence of color indicates more than about 20 million spermatozoa/mL and therefore a fertile sperm sample and the absence of color indicates less than about 20 million spermatozoa/mL and therefore a sub-fertile sperm sample. However, with regard to the necessarily more sensitive assays for indicating the efficacy of a male contraceptive, the presence of color indicates greater than about 100,000 spermatozoa/mL in the sample and therefor ineffective contraception; and the absence of color indicates less than about 100,000 spermatozoa/mL in the sample and therefore effective contraception.

In a second aspect, the invention features leukocyte screening assays, which are based on contacting a semen sample with an appropriate leukocyte specific reagent. In preferred embodiments, the leukocyte specific reagent is a peroxidase dependent color indicator and the presence of color indicates >1 million leukocytes/mL. and the absence of color indicates ≦1 million leukocytes/mL In a third aspect, the invention features diagnostic kits, comprised of a number of simple reagents packaged in a box. At a minimum, kits for determining male fertility or the efficacy of a male contraceptive, are comprised of an appropriate volume of a detectable sperm reagent; a substrate and instructions for use. At a minimum, kits for quantitating the number of leukocytes present in a semen sample are comprised of a defined volume of a leukocyte reagent; a substrate and instructions for use.

In a fourth and final aspect, the invention features improved methods for performing an Artificial Reproductive Technology (ART), based on identifying the most fertile sample from a donor using an assay described herein and utilizing that sample in an ART.

The instant disclosed kits are comprised of inexpensive reagents and the assays can be performed by most anyone in less than about 15 minutes' time. The information provided is useful, for example, to monitor the impact of changes in such factors as diet, sleep, exercise, exposure to smoke or other carcinogens, and intake of alcohol or drugs on the fertility of sperm samples produced thereafter. Also, the devices, kits and methods can indicate whether a particular male fertility or contraceptive treatment has been effective or whether sperm subsequently obtained from the same male is likely to initiate a pregnancy upon contact with an oocyte.

Other features and advantages will become readily apparent from the following Detailed Description and Claims.

BRIEF DESCRIPTION OF THE FIGURES

FIGS. 1A–1F are a schematic depiction of a preferred embodiment of the invention, wherein an appropriate volume of liquefied semen is transferred to a first well of a filter module (FIGS. 1A and 1B), so that sperm are retained on the filter and seminal plasma passes through (FIG. 1C); and a sperm reagent is added into the same well, (FIG. 1D) so that sperm reagent/sperm complexes are retained on the filter and excess sperm reagent passes through the filter (FIG. 1D), and the intensity of the sperm reagent on the filter provides an indication of the number of sperm on the filter (FIGS. 1E–1F).

DETAILED DESCRIPTION

Figure 2:
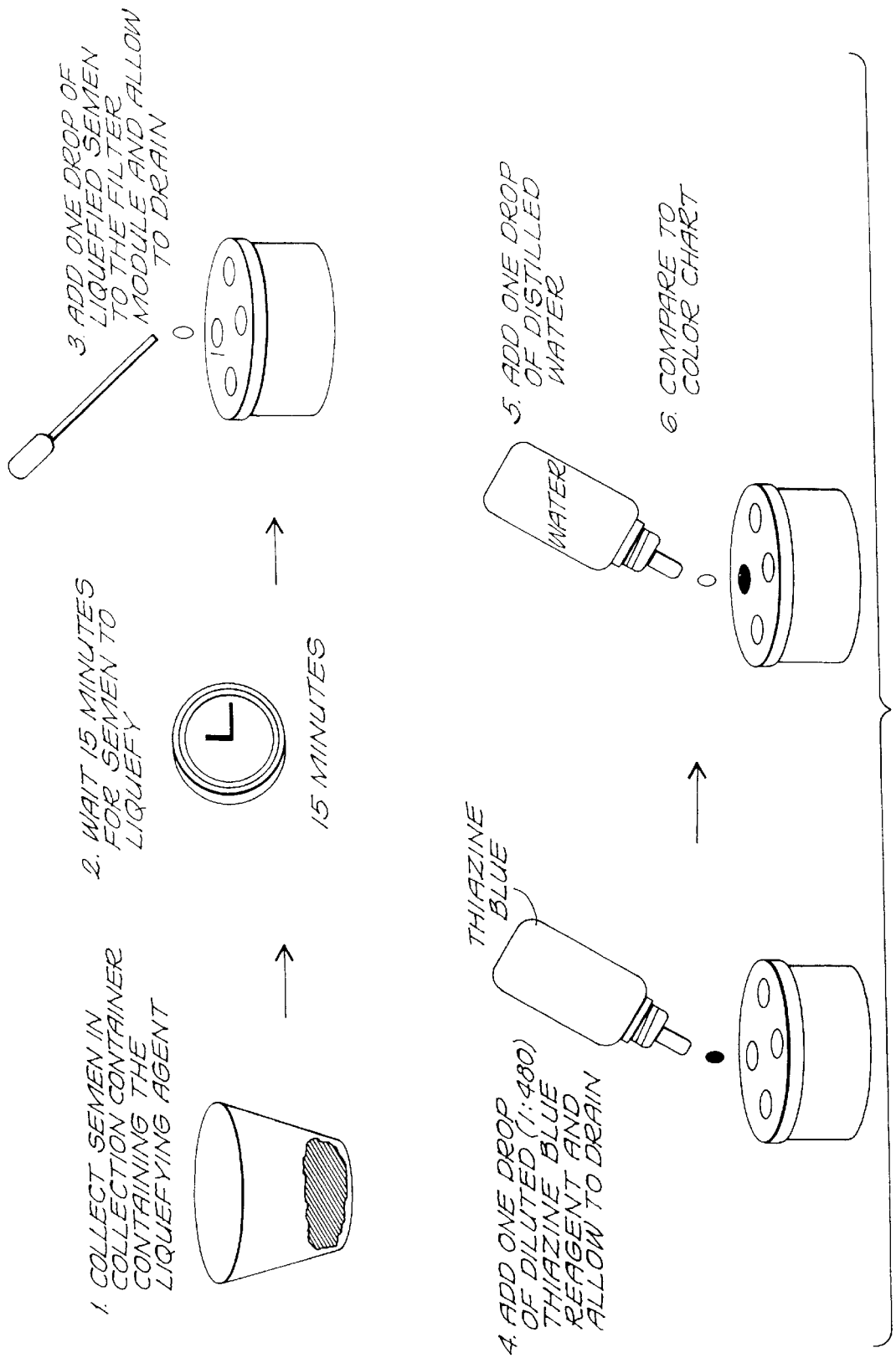
FIG. 2 is a schematic depiction of the steps performed using the FertilScreen™ kit for identifying the fertility potential of sperm samples.
Figure 3:
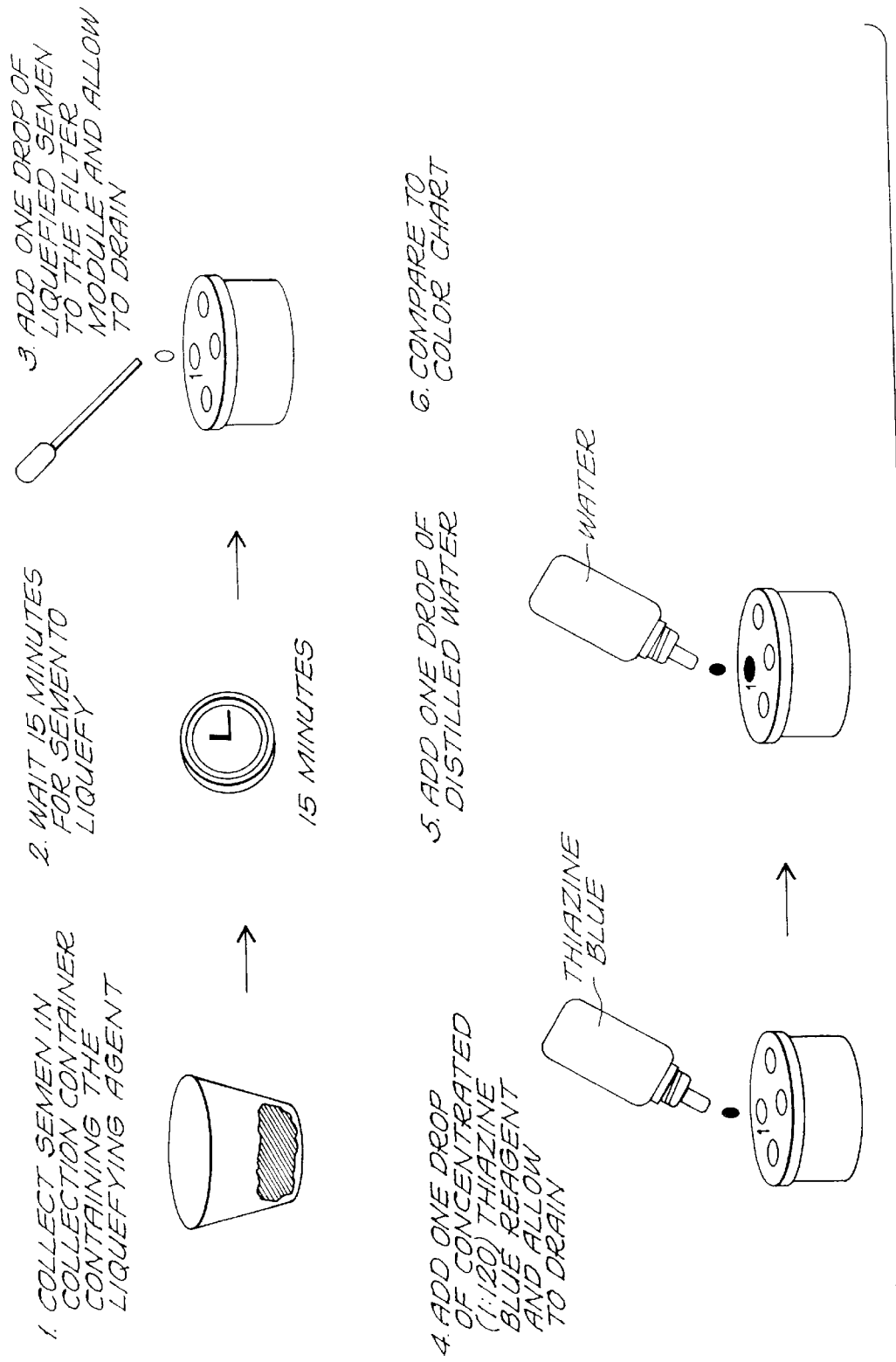
FIG. 3 is a schematic depiction of the steps performed using the VasScore ™ kit for determining the efficacy of a male contraceptive.
Figure 4:
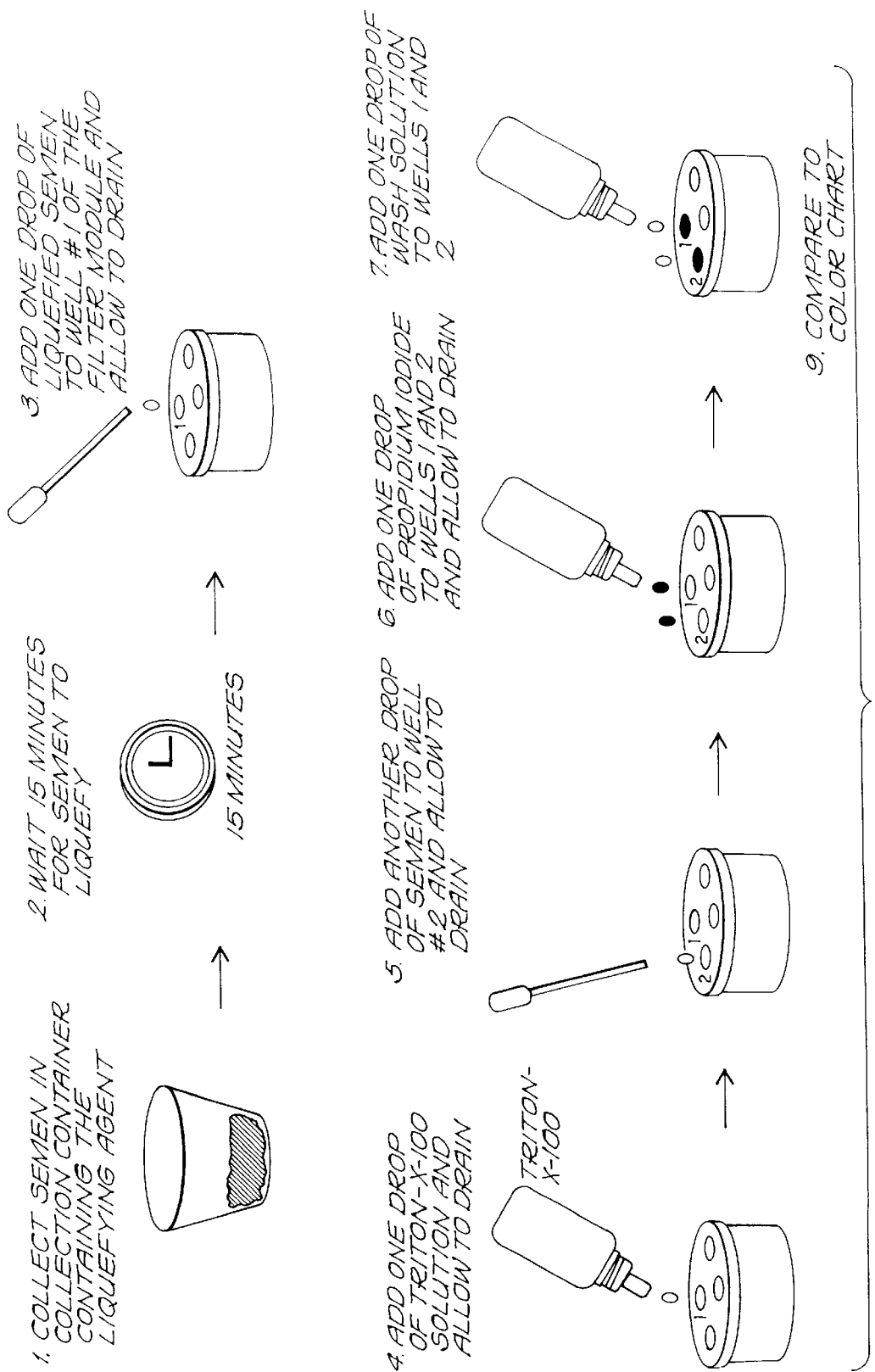
FIG. 4 is a schematic depiction of the steps performed using the VitalScore™ kit for determining sperm nuclear staining as an indication of sperm viability of a sperm sample.
Figure 5:
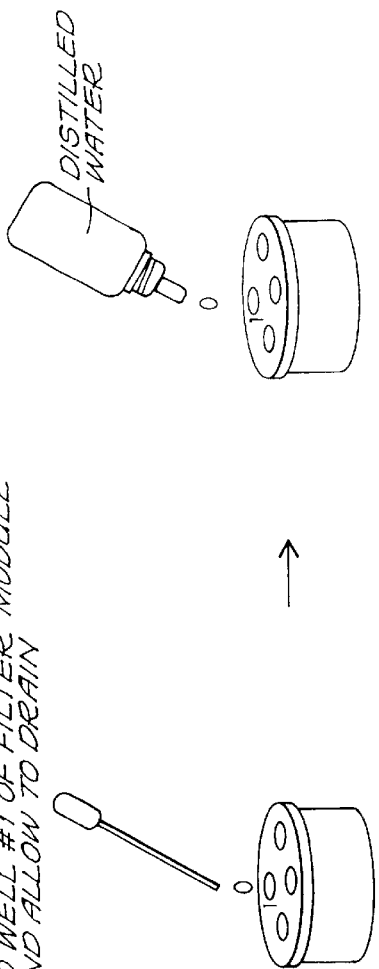
FIG. 5 is a schematic depiction of the steps performed using a kit for determining sperm superoxide dismutase activity as an indication of the fertility of a sperm sample.
Figure 6:
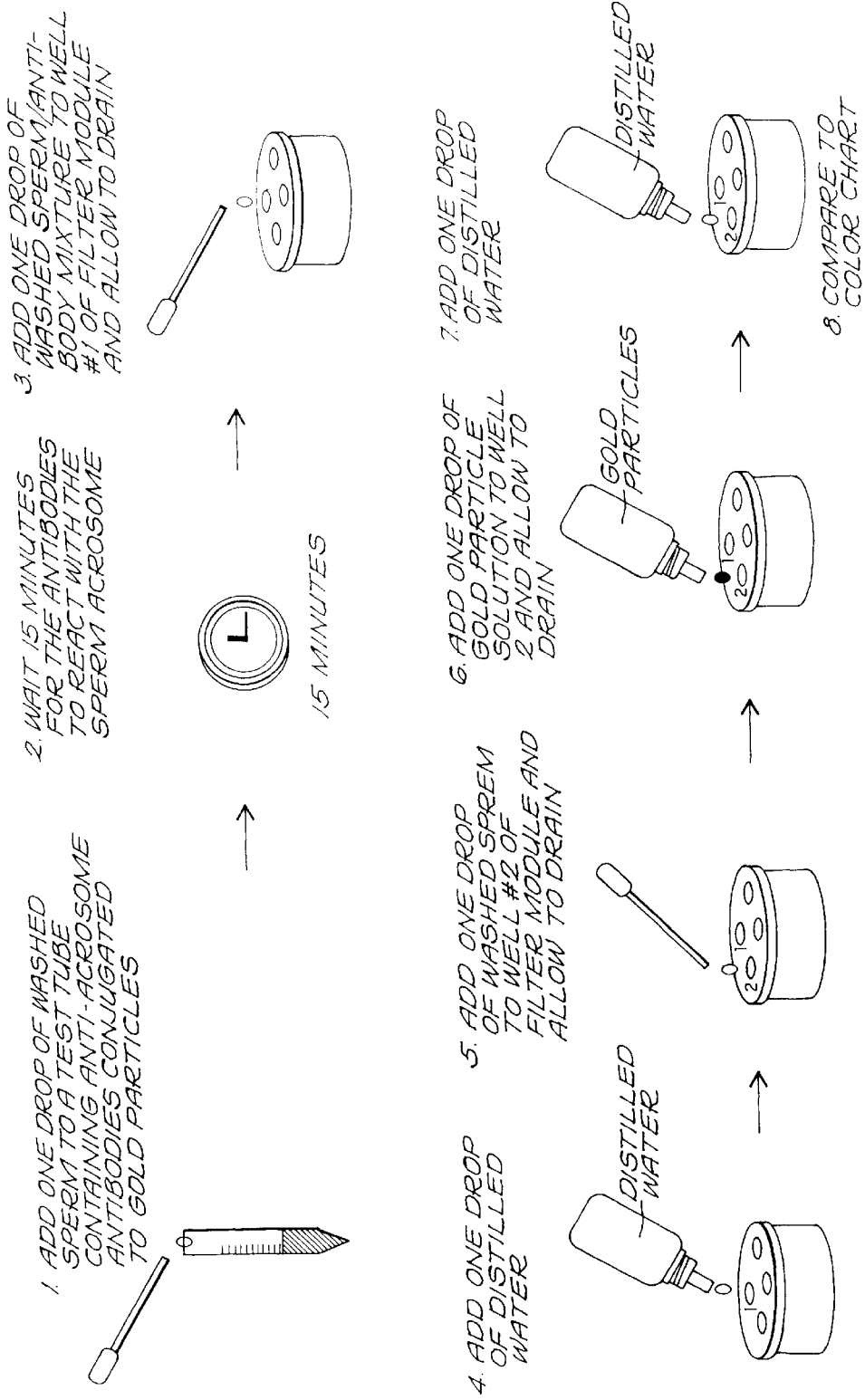
FIG. 6 is a schematic depiction of the steps performed using the AcroScreen™ kit for determining intact sperm acrosomes as an indication of the fertility of the sperm sample.
Figure 7:
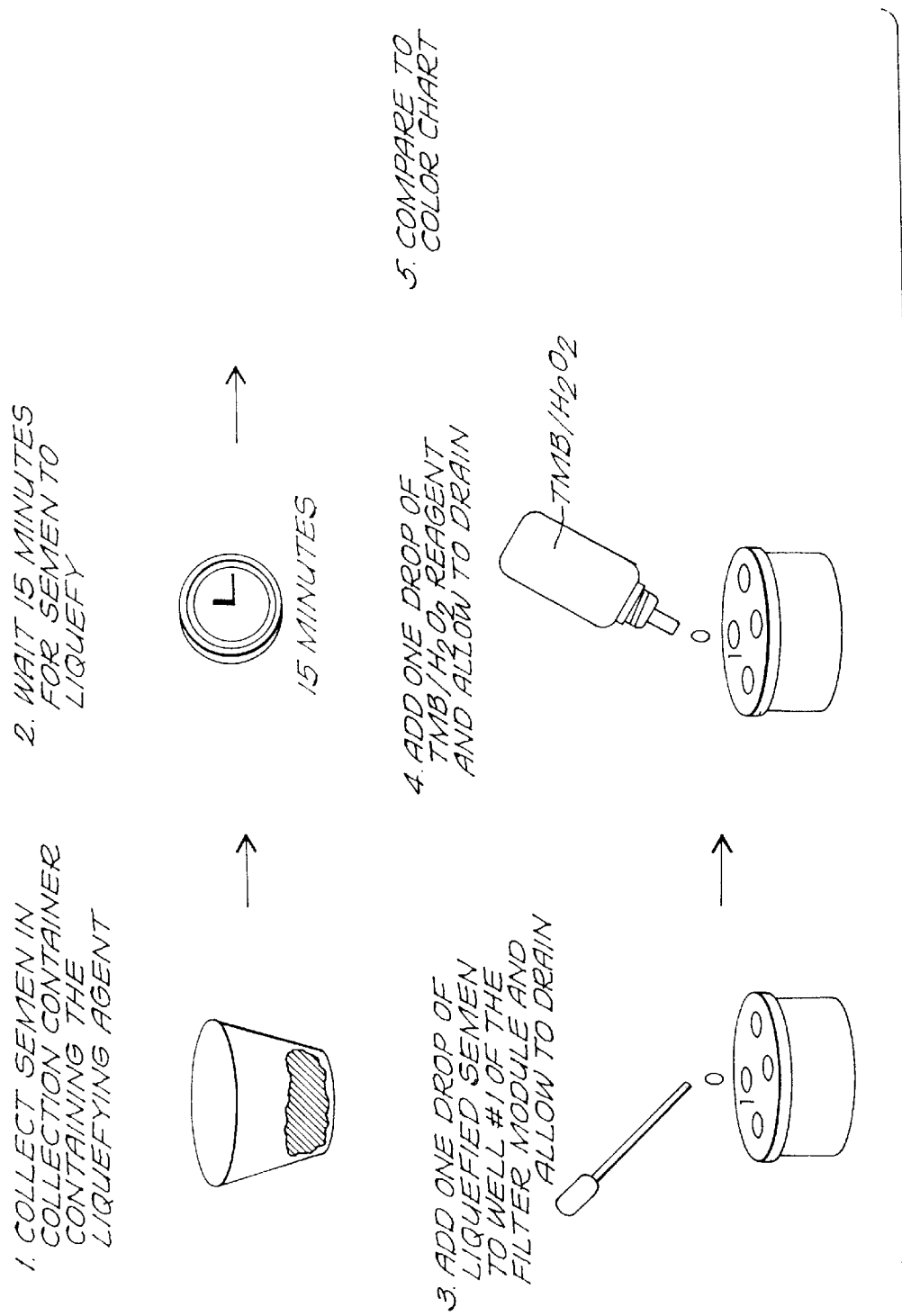
FIG. 7 is a schematic depiction of the steps to be performed using the LeukoScore™ kit for determining leukocyte count in a sperm sample.
Figure 8:
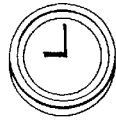
FIG. 8 is a schematic depiction of the steps to be performed using the ImmunoScore™ kit for determining sperm-bound antibodies in a sperm sample.
Figure 8:
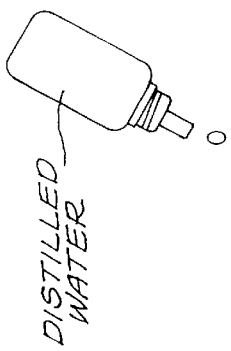
Figure 8:
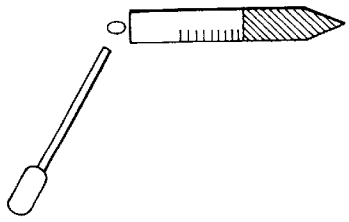
Figure 8:
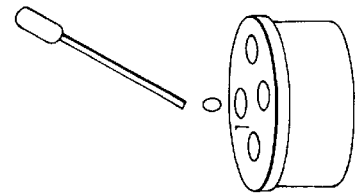

The invention features assays, which provide an indication of the fertility (e.g. ability to initiate a pregnancy) of a sperm containing sample. The invention also provides preferred kits for performance of the assays.

Preferred sperm containing samples (e.g. semen) to be analyzed in the disclosed assays are obtained from a human or animal (e.g. a bull, stallion, ram, dog or other domesticated animal or an endangered animal). To ensure accuracy, tests are preferably performed on freshly collected ejaculate; or "washed sperm" or seminal plasma-free sperm (i.e. sperm that has been substantially isolated from other semen components, e.g. by centrifugation or "swim-up).

As used herein, the term "fertile" refers to samples containing mostly motile and/or viable sperm and which therefore have a fairly high probability for initiating a pregnancy. The term "sub-fertile" refers to sperm samples, which contain non-motile or otherwise defective sperm and that therefore have a low likelihood of initiating a pregnancy. Once identified, fertile sperm samples can be used in an ART as described further below.

Identification of sub-fertile sperm samples is also useful, however, as a screen for detecting potentially infertile males. In addition, identification of a sperm sample as being sub-fertile is useful in confirming that a particular male contraceptive is effective or has taken effect. For example, a vasectomy typically requires a phase-in period in which to take effect. The use of the instant disclosed assays one to two weeks after the vasectomy and also at six months is important to rule out the occurrence of recanalization of the vas deferens.

An indication of the fertility potential of a sperm sample can be obtained based on quantifying the total number of sperm (non-motile and motile) in the sperm containing sample (e.g. ejaculate, semen or washed sperm). Preferably, sperm is quantified based on detecting the intensity of certain detectable sperm reagents as an indication of the concentration of sperm in the sample. Preferably, the detection can be performed by unaided observation. However, detections can also be aided or automated by instrumentation (e.g. a spectrophotometer, colorometer, fluorometer). If the number obtained is less than about 20 million spermatozoa/mL, the sperm sample is considered to be sub-fertile.

For determining whether a particular male contraceptive has been effective, the test must be particularly sensitive. For example, the VasScore™ test, which is described further in Example 3, can successfully distinguish colors based on a quantity of sperm protein that corresponds to a sperm concentration in the sample that is greater than or equal to about 100,000 spermatozoa/mL.

If the sperm sample is semen, it is preferred that the semen is liquefied prior to analysis. Although a semen sample will typically liquefy on its own at room temperature in about 30–60 minutes, preferably the semen sample is liquefied in less than 30 minutes and most preferably it is liquefied in 5–15 minutes, based on contact with a liquefaction reagent. Examples of appropriate liquefaction reagents include non-enzymatic reagents, such as dithiothreitol (DTT) (e.g. 1–5 mg/ml) and enzymes such as chymotrypsin and pronase (e.g. 5–15 mg/ml.)

Preferred methods for determining sperm fertility potential involve quantitating a particular sperm target or component as an indication of the number of sperm present in a sperm containing sample. Examples of appropriate targets or components include sperm proteins (e.g. sperm flagellar proteins, glycolytic enzymes, antioxidant enzymes (e.g. glutathione peroxidase or superoxide dismutase), nuclear proteins, acrosomal proteins, α-tubulin, lactate dehydrogenase (LDH-X), protamine (sperm histones), acrosomal proteins (e.g. acrosin) or mitochondrial proteins); sperm lipids (e.g. cholesterol, phospholipids, glycolipids, triglycerides, phosphatidylglycerols, seminolipids, and fatty acids, particularly docosahexaenoic acid, which is one of the few fatty acids found in sperm); nucleic acids or a mixture of sperm components (e.g. thiazine blue reacts with sperm proteins, lipids and other sperm components). Preferred targets for sperm quantitation are selective for and/or abundant on sperm cells.

Preferably a sperm reagent (e.g. sperm antibody, ligand, lectin, substrate or specific dye) is used to quantitate sperm. Preferably after contacting a sperm sample with a detectable sperm reagent, the mixture is deposited onto a substrate for detection. In a preferred embodiment, which is shown in FIG. 1, the substrate is a filter of an appropriate porosity so that sperm, including sperm that is complexed to (e.g. interacting with) sperm reagent are retained on the filter and uncomplexed sperm reagent passes through the filter.

Preferred sperm reagents include labeled (e.g. dye or tracer labeled) or unlabeled reagents that specifically stain based on interaction with a sperm component (e.g. sperm protein, sperm lipid, sperm nucleic acid, sperm carbohydrate and/or other sperm component (e.g. mitochondria, nucleus). For example, Protein Reagent (0.3% tetrabromophenol, Miles Scientific, Connecticut colors sperm based on interaction with sperm protein. Rhodamine 123 colors sperm by accumulating within sperm mitochondria. Detectably labeled protein A specifically colors sperm by binding to sperm bound antibodies. Propidium iodide and eosin specifically color sperm by interactng with sperm nucleic acids. However, both reagents can only diffuse into cells, which have been permeabilized (e.g. using a detergent). Acridine orange, on the other hand, can specically color unpermeabilized sperm based on interaction with decondensed sperm chromatin (but not condensed sperm chromatin). Sperm chomatin can be decondensed prior to staining with acridine orange by reducing sperm protamines (i.e. sperm histones).

A preferred reagent for reducing sperm protamines is dithiothreitol (DTT). Other reagents, which specifically interact with a semen or washed sperm sample, include gold particles (which have an intrinsic pink color and react with proteins) thiazine blue, tetrabromophenol and rhodamine (red-colored and reacts with lipids).

Other preferred sperm reagents include sperm antibodies, such as labeled (e.g. enzyme, tracer (e.g. radioactive), dye or color particle labeled) or unlabeled anti-sperm antibodies (e.g. anti-human sperm polyclonal antibody; Arnel Products Co., Inc, Cherokee Station, New York, N.Y.; Chemicon International Inc., Temecula, Calif.) or labeled or unlabeled antibodies against a sperm component (e.g. a sperm protein or sperm lipid). Preferred antibodies include anti-human sperm polyclonal antibodies and antibodies specific to an epitope of the sperm flagellum, nuclear proteins, glycolytic enzymes, acrosome etc.). As used herein, the term "antibody" refers to any material that binds an antigen (e.g. polyclonal, monoclonal or single chain antibody or antibody fragment, such as an Fab of Fab'$_2$ fragment).

One method for quantitating sperm involves incubating a sperm sample with colored particles containing anti-sperm antibodies for an appropriate period of time to allow the sperm antigens to react with the antibody bound colored particles; ii) filtering the sample of step i), so that sperm/colored particle/antibody complex is retained on the filter and unbound, colored particle/antibody and seminal plasma protein passes through the filter; and iii) visualizing the color intensity on the filter as an indication of the number of sperm on the filter. For example, if colored particles are used, sperm/colored particle/antibody complexes can be quantitated by comparing the color of the filter to a color chart, which depicts various color possibilities for various quantities of sperm.

Alternatively, the filter membrane can be configured to indicate a "+" (i.e. fertility), if a sufficient amount of sperm/detectable particle/antibody complex is retained on the filter membrane to indicate that the sample is suitable for initiating a pregnancy greater than about 20 million spermatozoa/mL) and a "−" (i.e. sub-fertile) if an insufficient amount of sperm/detectable particle/antibody complex is retained on the filter membrane (less than about 20 million spermatozoa/mL).

In order to use antibodies or reagents that may also react with seminal plasma components present in a sperm containing sample (e.g. ejaculate), sperm can first be isolated. Seminal plasma-free sperm can then be contacted with anti-sperm antibody coated colored particles. After a sufficient period of time to allow antibodies and antigens to react, unbound antibody coated colored particles can be removed from the mixture and sperm/colored particle/antibody complex detected and quantitated. For example, the quantity of sperm in the sample can be quantitated using a color chart or a "+" or "−" filter as described above. Alternatively, sperm can be quantitated by detecting the appearance of agglutination in a drop of sample following addition of anti-sperm antibodies with bound latex particles.

Immunodetection of an antigenic indicator of sperm in a sample can be accomplished using any of a number of competitive or non-competitive assay procedures. In general, competitive immunoassays are performed by adding the antigen to be detected to a sperm containing sample, so that the sperm and the antigen compete for a limited number of antibody binding sites resulting in the formation of sperm-antibody and labeled antigen-antibody complexes. By maintaining the concentration of labeled antigen and antibody constant, the amount of labeled antibody complex formed is inversely proportional to the amount of sperm present in the sample. A quantitative determination of the sperm can therefore be made based on the labeled antibody complex. Competitive assays can be homogeneous (i.e. not requiring separation of antibody bound tracer (e.g. labeled antigen) from free tracer, since the antigen-antibody interaction causes, directly or indirectly, a measurable change in the signal obtained from the label group of the tracer). Alternatively, competitive assays can be heterogeneous (i.e. requiring separation of bound tracer from free tracer prior to determining the amount of ligand in the sample).

In contrast to competitive immunoassays, non-competitive assays involve incubating a sperm containing sample with an immobilized sperm antibody for a period of time sufficient to reach equilibrium with regard to the formation of antibody-sperm conjugates. The sperm antibody can be directly or indirectly labeled. For example, indirect labeling can be carried out after a wash step to remove unbound sperm by contacting the immobilized antibody-sperm complexes with a second, labeled antibody that is specific for the antibody-sperm complex. Following a second wash step to remove unbound second antibody, the amount of bound second antibody can be detected and measured as an indication of bound sperm.

Exemplary competitive and non-competitive immunoassays include fluorescence polarization immunoassay (FPIA), fluorescence immunoassay (FIA), enzyme immunoassay (EIA), nephelometric inhibition immunoassay (NIA), enzyme linked immunosorbent assay (ELISA) and radioimmunoassay (RIA). General techniques for performing the various immunoassays are known to one of skill in the art. Moreover, a general description of most procedures is provided in U.S. Pat. No. 5,051,361, which is incorporated herein by reference. The antibodies can be labeled in any manner that facilitates detection. Preferred labels include enzymes (e.g. horseradish peroxidase, alkaline phosphatase, urease, β-galactosidase), enzyme co-factors, radioisotopes (e.g. $^3H$, $^{14}C$, $^{125}I$, $^{32}P$, $^{131}I$ and $^{35}S$), fluorescent compounds (e.g. fluorescein, rhodamine, allophycocyanin, phycoerythin, erythrosin, europian, luminol, luciferin and coumarin) and colored or uncolored beads or particles (e.g. silica gel, controlled pore glass, magnetic, Sephadex/Sepharose, cellulose, metal (e.g. gold) or latex). Preferred supports for immobilizing antibodies include membranes (e.g. polyethylene, polypropylene, polyamide, polyvinylidenedifluoride, glass fiber, paper), beads or particles and tubes, (e.g., glass, plastic or metal capillaries, straws or pipettes).

In addition to providing assays that employ a sperm reagent to determine potential fertility, the invention also provides assays that employ leukocyte reagents to determine the number of leukocytes present in a semen sample, which can also impact potential fertility. For example, leukocyte infiltration in semen is frequently associated with genitourinary infection, antisperm antibodies and male infertility.

Preferred assays for screening for leukocytes are based on contacting the semen sample with an appropriate amount of a leukocyte reagent (i.e. a reagent that interacts with leukocytes, but not other semen components) and detecting the color as an indication of the quantity of leukocytes in the semen sample. Since leukocytes contain myeloperoxidases, which can react with a peroxidase dependent color reagent; while sperm contain a different peroxidase (glutathione peroxidase), which will not react with a peroxidase dependent color reagent; a preferred leukocyte reagent is a peroxidase dependent color indicator. In a particularly preferred embodiment, the peroxidase dependent color indicator is tetramethylbenzidene/hydrogen peroxide (TMB/$H_2O_2$) and the presence of blue color indicates >1 million leukocytes/ml, and the absence of color indicates ≦1 million leukocytes/mL.

In another aspect, the invention features sperm diagnostic kits or systems comprising a number of simple reagents and devices packaged in a box. Preferable kits for home use include reagents for liquefying semen (enzymatic or non-enzymatic). It is preferred that a non-enzymatic reagent be used to prepare semen for tests involving detection of sperm proteins (e.g. OptiSperm™, Acroscreen™ or ImmunoScore). Reagents and devices for use in determining sperm fertility can include dispensing devices (e.g. droppers, capillaries or pipettes) for delivering a defined volume of liquefied semen or washed sperm from a collection container (e.g. a condom) into a substrate containing container to which a sperm or leukocyte reagent is added. The kit also preferably includes a color chart and instructions for use.

Based on the above-described procedures for identifying potentially fertile sperm samples, the invention also features processes for increasing the success rate for initiating a pregnancy using an assisted reproductive technology (ART) (i.e. a procedure for contacting a sperm with an ovum to initiate a pregnancy). Examples of ARTs include in vitro fertilization (IVF), gamete intrafallopian transfer (GIFT) intrauterine insemination (IUI) and intracytoplasmic sperm injection (ICSI). Procedures for performing ARTs are well-known to practitioners. It is expected that additional ARTs will be developed over time.

A preferred process of the invention involves obtaining multiple sperm samples from a donor (e.g. a male partner from a couple undergoing an ART) over time.

For example, a donor can provide a new sperm sample once every other day. An aliquot (e.g. $1 \times 10^6$ cells) of each sample can then be obtained for testing, while the remainder can be banked (e.g. cryopreserved) for potential future use in an ART. Preferably the process includes a means for correlating a particular aliquot with the banked sample from which it was obtained. For example, an aliquot taken from a sample, as well as the sample itself obtained on day 1 can be labeled #1. A subsequently obtained sample from the same donor and an aliquot taken from that sample can be labeled #2, etc.

All aliquots provided by a particular donor can then be tested using the assays described herein to identify fertile sperm samples (e.g. samples having a greater than 50% probability of initiating a pregnancy upon contacting an oocyte). A sperm sample indicated as being highly fertile can then be used in an ART and the remaining samples can be discarded.

The present invention is further illustrated by the following Examples which are intended merely to further illustrate and should not be construed as limiting. The entire contents of all of the references (including literature references, issued patents, published patent applications, and co-pending patent applications) cited throughout this application are hereby expressly incorporated by reference.

EXAMPLE 1

Assay For Determining Sperm Count in Semen (FertilScreen™)

This assay is particularly useful for screening of male factor infertility at home, a physician's office or at an andrology lab. The kit can also be used for research purposes, e.g. as a semiquantitative assay to determine sperm count in semen.

Kit Components 1) (1) collection container containing about 10 mg of lyophilized chymotrypsin (optional);
2) (1) dropper;
3) (1) filter module [e.g. Progene Corporation, cat # 000012]
4) (1) container containing at least one drop of thiazine blue reagent (diluted 1:480)
5) (1) container containing at least one drop of $dH_2O$;
6) instructions for use.

Procedure

Semen was collected in the collection container containing chymotrypsin. The mixture was allowed to stand at room temperature for about 15 minutes in order for the semen to liquefy (optional step).

Using a dropper, one drop of liquefied semen was added to the filter module. After the liquid had drained, one drop of the thiazine blue reagent (diluted 1:480) was added to the filter module. After the liquid had drained, one drop of distilled water was added to the filter module.

The color of the module was then observed. The presence of a blue color corresponded to a sperm concentration in semen $\geq 20$ million/ml (indicating a potentially fertile sperm sample) and the absence of color to <20 million/ml (indicating a sub-fertile sperm sample).

Study

The objectives of this study were (1) to evaluate the performance of the novel FertilScreen™ kit in the determination of sperm count in semen, as compared to microscopic analysis and (2) to determine the efficacy of the FertilScreen™ kit in screening male factor infertility.

A total of 125 semen samples were obtained from 125 males presenting for infertility screening. Aliquots of the liquefied semen were scored for sperm count and percent motility by microscopic analysis. Sperm count in semen was also determined using the FertilScreen™ kit as follows: 50 μl of the liquefied semen was added to a 3 mm-diameter well in a plastic module and allowed to drain through a filter sandwiched in the plastic module. Then 50 μl of the thiazine blue reagent was added and the filter rinsed with 50 μl of the kit wash solution. The absence of color on the filter was considered a negative test (<20 million/ml) and the presence of blue color was considered a positive test ($\geq 20$ million/ml).

Of the 125 samples evaluated by microscopic analysis, 89 had sperm counts $\geq 20$ million/ml and 36 had counts <20 million/ml. All 89 samples with counts $\geq 20$ million/ml were correctly identified as positive by the kit. Of the 36 samples with counts <20 million/ml, 34 were correctly identified as negative and 2 were incorrectly identified as negative. Sperm count in these two samples were 18 million/ml and 19 million/ml, respectively, as determined by microscopic analysis. The sensitivity and specificity of the FertilScreen™ kit for sperm count in semen at the 20 million/ml cutoff were 100% and 98%, respectively. Of the 125 males evaluated, 45 (36%) were diagnosed with male factor infertility based on a sperm count <20 million/ml, a percent motility <50%, or sperm agglutination, as determined by microscopic analysis. Of these 45 males, 36 (80%) had counts <20 million/ml, and 9 (20%) had counts $\geq 20$ million/ml. The FertilScreen™ kit correctly identified 76% of all male factor infertility cases and 95% of the samples with counts <20 million/ml. Total test kit time was 2 minutes. In conclusion, the FertilScreen™ kit could be used as a reliable test for the screening of male factor infertility in the physician's office and potentially at home.

EXAMPLE 2

Assay For Determining Sperm Count in Washed Sperm (SpermCount.™)

This assay is particularly useful for obtaining sperm count (e.g. as an indication of male factor infertility) at an andrology lab or sperm bank.

Kit Components 1) (1) dropper;
2) (1) filter module [e.g. Progene Corporation, cat # 000012];
3) (1) container containing at least one drop of colloidal gold solution;
4) (1) container containing at least one drop of $dH_2O$;
5) color chart (in which each of the color intensities depicted in the chart corresponds to a sperm concentration from about 5 million to about 100 million/ml at 10 million/ml intervals); and
6) instructions for use.

Procedure

Using a dropper, one drop of washed sperm (i.e. sperm that had been isolated from semen by centrifugation) was added to a well of the filter module. After the liquid had drained, one drop of the colloidal gold solution was added to the well. After the liquid had drained, one drop of distilled water was added to the well.

The color intensity in the well of the module was then observed and compared with the color chart to determine the sperm concentration in the sample.

EXAMPLE 3

Assay For Determining Efficacy of a Vasectomy (VasScore™)

This assay is particularly useful as a home kit to monitor the efficacy of a vasectomy. Preferably, the vasectomized male uses the kit one to two weeks after the vasectomy and also after six months to rule out the occurrence of recanalization of the vas deferens.

Kit Components 1) (1) collection container containing about 10 mg of dried chymotrypsin (optional);
2) (3) droppers;
3) (1) filter module [e.g. Progene Corporation, cat # 000012]
4) (1) squeeze bottle containing at least one drop of thiazinc blue reagent (diluted 1:120)
5) (1) squeeze bottle containing at least one drop of $dH_2O$;
6) instructions for use.

Procedure

Semen was collected in the collection container containing chymotrypsin. The mixture was allowed to stand at room temperature for about 15 minutes in order for the semen to liquefy (optional step).

Using a dropper, one drop of the liquefied semen (or optionally washed sperm) was added to a well of the filter module. After the liquid had drained, one drop of the thiazine blue reagent was added to the same well. After the liquid had drained, one drop of $dH_2O$ was added to the filter module.

The color of the module was then observed. The presence of blue color corresponded to a sperm concentration in semen of about $\geq 0.1$ million/ml (indicating that the vasectomy may not have been effective) and the absence of color to a sperm concentration of about <0.1 million/ml. (indicating that the vasectomy was effective).

Study

A vasectomy is considered successful when no sperm are found in the ejaculate, as determined by microscopic analysis. A semen analysis is usually performed in vasectomized males about six weeks after the vasectomy. However, some vasectomized males may produce a sperm-free ejaculate as early as one week after the vasectomy. In addition, vasectomized males are encouraged to repeat a semen analysis six months after the vasectomy to rule out the occurrence of recanalization of the vas deferens.

The objective of this study was to evaluate the performance of the VasScore ™ test kit in the determination of very low sperm counts in semen, as compared to microscopic analysis. A total of 65 semen samples were obtained from 50 males presenting for infertility screening and from 15 males that underwent vasectomy.

Aliquots of the liquefied semen were scored for sperm count by microscopic analysis. Sperm count in semen was also determined using the VasScore™ kit as follows: 100 μl of the liquefied semen was added to a 3 mm-diameter well in a plastic module and allowed to drain through a filter sandwiched in the plastic module. Then, 100 μl of the VasScore™ reagent (i.e. thiazine blue reagent (diluted 1:120)) was added and the filter rinsed with 100 μl of the wash solution. The absence of color on the filter was considered a negative test (<100,000/ml) and the presence of blue color was considered a positive test ($\geq$100,000/ml).

Of the 65 samples evaluated by microscopic analysis, 15 had sperm counts <100,000/mi (0 to 100/ml) and 50 had sperm counts $\geq$100,000/ml (300,000 to 2 million/ml). All 15 samples with counts <100,000/ml were correctly identified as negative by the VasScore™ kit and all 50 samples with counts >100,000 were correctly identified as positive by the VasScore™ kit. The sensitivity and specificity of the VasScore™ kit at the selected cutoff point was 100%. Total test kit time was 2 minutes. These results indicate that the VasScore™ kit is a simple and reliable test for the determination of very low sperm counts in semen. Furthermore, the VasScore™ kit could potentially be used as a home kit to better assess the time for the final visit to the urologist to confirm the presence of a sperm-free ejaculate or to monitor the occurrence of recanalization of the vas deferens.

EXAMPLE 4
Assay For Determining Sperm Viability (VitalScore™)

This assay is particularly useful to monitor sperm fertility/motility at a physician's office, andrology lab, veterinary office or animal farm. In addition the test can be used to determine the fertility of semen samples obtained from farm animals, e.g., horse, bovine, porcine. Further the test can be used in research as a semiquantitative assay of sperm viability/motility Kit Components
1) (1) collection container containing about 10 mg of lyophilized chymotrypsin (optional);
2) (2) droppers;
3) (1) filter module [e.g. Progene Corporation, cat # 000012];
4) (1) container containing at least one drop of 0.1% Triton X-100 solution in dH$_2$O;
5) (1) container containing at least one drop of propidium iodide (1mg/ml);
6) (1) (or optionally 2) squeeze bottle(s) containing at least two drops of dH$_2$O;
7) a color chart (in which each of the color intensities depicted in the chart correspond to sperm concentrations from about 5 million to about 100 million/ml at 10 million/ml intervals); and
8) instructions for use.

Procedure

Semen was collected in the collection container containing chymotrypsin. The mixture was allowed to stand at room temperature for about 15 minutes in order for the semen to liquefy (optional step).

Using a first dropper, one drop of the liquefied semen (or optionally washed sperm) was added to a first well of the filter module. After the liquid had drained, one drop of 0.1% Triton X-100 solution in dH$_2$O was added to the same well.

Using a second dropper, one drop of the liquefied semen (or optionally washed sperm) was added to a second well of the filter module. After the liquid had drained from both the first and second wells, one drop of propidium iodide (1mg/ml) was added to wells #1 and #2. After the liquid had drained from both wells, one drop of dH$_2$O was added to each well.

The color intensity observed in each well was then compared to the color chart. To obtain the number of motile sperm in the sample, the concentration obtained in well #2 was subtracted from the concentration obtained in well #1. For example, if the color intensity in well #1 corresponded to 50 million sperm/ml and that in well #2 to 10 million sperm/ml, the total number of motile cells corresponded to 40 million sperm/ml or 80% motility.

EXAMPLE 5
Test kit For Determining Superoxide Dismutase (SOD) Immunoreactivity in Sperm (OptiSperm™)

This assay is useful for determining the fertility potential of a sperm sample. The assay is preferably performed in a physician's office, sperm bank or andrology lab.

Kit Components
1) (1) collection container (optional);
2) (1) dropper;
3) (1) filter module [e.g. Progene Corporation, cat # 000012];
4) (1) container containing at least one drop of anti-SOD antibody bound gold colloidal solution;
5) (1) container containing at least one drop of dH$_2$O;
6) a color chart; and
7) instructions for use.

Procedure

If semen was collected in a collection container, the semen was allowed to stand at room temperature for about 30 minutes in order for the semen to liquefy (optional).

Using a first dropper, one drop of the liquefied semen (or optionally washed sperm) was added to a well of the filter module. After the liquid had drained, one drop of anti-SOD antibody bound colloidal gold solution was added to the same well. After the liquid had drained from the well, one drop of dH$_2$O was added to the same well of the filter module.

The color intensities in the well was then observed and compared to the color chart, wherein the presence of a bright pink color corresponds to high SOD immunoreactivity; the absence of color to low SOD and faint color to borderline SOD immunoreactivity.

EXAMPLE 6
Test kit to Determining Acrosome Intact Sperm (AcroScreen™)

This assay is useful to assess the fertility potential of sperm in semen or in washed sperm at a physician's office, andrology lab, or animal farm. The kit can also be used for research purposes to provide a semiquantitative assay of fertile/motile sperm.

Kit Components
1) (1) collection container (optional);
2) (3) droppers;
3) (1) test tube containing anti-acrosome antibody bound gold colloidal solution;
4) (1) container containing at least one drop of gold colloidal solution;

5) (1) filter module [e.g. Progene Corporation, cat # 000012];
6) (1) container containing at least one drop of $dH_2O$;
7) a color chart; and
8) instructions for use.

Procedure

If semen was used, semen was collected in the collection container and allowed to stand at room temperature for about 30 minutes in order for the semen to liquefy (optional step).

Using a first dropper, one drop of the liquefied semen (or washed sperm) was added to a test tube containing anti-acrosome antibody bound gold colloidal solution. After allowing sufficient time for the antibodies to react with sperm acrosomes (about 10 minutes), using a second dropper, one drop of the sperm/antibody mixture was added to a first well (well #1) of the filter module. After the liquid had drained, one drop of $dH_2O$ was added to the same well (well #1) of the filter module.

Using a third dropper, one drop of the liquefied semen (or washed sperm) was added to a second well (well #2) of the filter module. After the liquid had drained, one drop of colloidal gold solution was added to the same well. After the liquid had drained again, one drop of $dH_2O$ was added to the same well (well #2) of the filter module.

The color intensities in the wells were then observed and compared to the color chart. By substracting the sperm concentration obtained in well #1 from that obtained in well #2, the concentration of sperm with intact acrosomes is determined.

EXAMPLE 7

Assay For Determining Leukocyte Count in Semen (LeukoScore™)

This assay is useful to determine leukocyte count in human or animal semen at a physician's office, andrology lab or farm. A leukocyte count in semen greater than 1 million/ml is diagnostic of leukocytospermia by WHO criteria. The test can also be used as a semiquantitative assay for research purposes.

Kit Components 1) (1) collection container containing about 10 mg of lyophilized chymotrypsin;
2) (1) dropper;
3) (1) filter module [e.g. Progene Corporation, cat # 000012];
4) (1) container containing at least one drop of tetramethylbenzidine $H_2O_2$ (TMB) in dimethylformamide (Diatech Inc., Allston, Mass.) "$TMB/H_2O_2$ reagent";
5) a color chart (in which each of the color intensities depicted in the chart corresponds to a sperm concentration from 0 to 10 million/ml at 0.5 million /ml intervals); and
6) instructions for use.

Procedure

Semen was collected in the collection container containing chymotrypsin. The mixture was allowed to stand at room temperature for about 15 minutes in order for the semen to liquefy.

Using a first dropper, one drop of the liquefied semen was added to a well of the filter module. After the liquid had drained, one drop of $TMB/H_2O_2$ reagent was added to the same well.

The color intensities observed in the well is then observed and compared to the color chart, wherein the presence of blue color corresponds to >1 million leukocytes/ml and the absence of color to ≦1 million/ml.

Study

The objective of this study was to evaluate the performance of the novel LeukoScore™ kit in the determination of leukocyte count in semen, as compared to brightfield microscopy.

A total of 128 semen samples were obtained from 128 males presenting for an infertility diagnosis. Aliquots of 50 μl of the liquefied semen were mixed with 200 μl of a solution of tetramethylbenzidine $H_2O_2$ (TMB) in dimethylformamide (Diatech Inc., Allston, Mass.), incubated at room temperature for 2 minutes and the number of peroxidase-positive cells exhibiting a blue color scored by brightfield microscopy. Leukocyte count in semen was also determined using the LezkoScore™ kit as follows: 50 μl of the liquefied semen was added to a 3 mm-diameter well in a plastic module and allowed to drain through a filter (2.7 μm in pore size) sandwiched in the plastic module, followed by addition of 50 μl of the TMB reagent.

The absence of color on the filter following addition of the TMB reagent was considered a positive test (>1 million/ml). Of the 128 samples evaluated, 32 had leukocyte counts >1 million/ml (1 to 3 million/ml) and 96 had counts ≦1 million/ml were correctly identified as negative by the LeukoScore™ kit. Of the 32 samples with counts >1 million/ml, 31 were correctly identifed as positive and 1 was incorrectly identified as negative. Leukocyte count in this sample was 0.90 million/ml. The sensitivity, specificity and positive and negative predictive values of the LeukoScore™ kit for leukocyte count at the 1 million/ml cutoff point were 100%, 99%, 97% and 100%, respectively. Total test kit time was 1 minute. These results indicate that the LeukoScore™ kit could be used as a convenient and reliable test for the diagnosis of leukocytospermia in semen in the andrology laboratory, in the physician's office and potentially at home.

EXAMPLE 8

Assay For Determining Anti-Sperm Antibodies (ImmunoScore™ and EquiImmunoScore™)

This assay is useful to screen for anti-sperm antibodies in human or horse semen at a physician of veterinarian's office or at an andrology lab or horse farm. Further the test can be used in research as a semiquantitative assay of sperm fertility/motility.

Kit Components 1) (1) collection container (optional);
2) (1) dropper;
3) (1) filter module [e.g. Progene Corporation, cat # 000012];
4) (1) container containing at least one drop of protein A bound colloidal gold solution.
5) (1) container containing at least one drop of $dH_2O$; and
6) instructions for use.

Procedure

Semen was collected in the collection container and allowed to stand at room temperature for about 30 minutes in order for the semen to liquefy.

Using a first dropper, one drop of the liquefied semen was added to a well of the filter module. After the liquid had drained, one drop of protein A bound colloidal gold solution was added to the same well. After the liquid had drained from the well, one drop of $dH_2O$ was added to the same well of the filter module.

The color intensities observed in the well is then compared to the color chart, wherein in an increasingly dark pink color corresponds to a greater concentration of sperm bound antibodies and a very light pink color corresponds to no or very little sperm bound antibodies.

EXAMPLE 9

Triple Test Semen Analysis Kit

Kit Components 1) (1) collection container containing about 10 mg of lyophilized chymotrypsin;

2) (1) multipipette;
3) (1) 12-well dot blot cartridge (e.g. 4"×3");
4) (1) container containing at least 4×50 µl of 0.1% Triton X-100 solution in phosphate buffered saline (PBS);
5) (1) container containing at least 8×50 µl of propidium iodide (1 mg/ml) in phosphate buffered saline (PBS);
6) (1) container containing at least 4×50 µl of tetramethylbenzidine $H_2O_2$ (TMB/$H_2O_2$) in dimethylformamide (Diatech Inc., Allston, Mass.) "TMB/$H_2O_2$ reagent";
7) (1) container containing at least 12×50 µl of d$H_2O$;
8) a color chart or densitometer; and
9) instructions for use.

Procedure

Semen was collected in the collection container containing chymotrypsin. The mixture was allowed to stand at room temperature for about 15 minutes in order for the semen to liquefy.

Using the multipipette, 50 µl of the liquefied semen was added to each well of the dot blot cartridge; 50 µl of 0.1% Triton X-100 solution in PBS and 50 µl of propidium iodide in PBS (1 mg/m) was added to all four wells in the top row (A); 50 µl of propidium iodide in PBS (1 mg/ml) was also added to all four wells in the middle row (B); and 50 µl of tetramethylbenzidine $H_2O_2$ (TMB) in dimethylformamide was added to all four wells in the bottom row (C). 50 µl of d$H_2O$ was then added to all twelve wells using a micropipette. Rows A and B were used to obtain sperm count and the number of permeabilized sperm (fertile sperm) respectively; and row C was used to determine leukocyte count in semen.

The color intensities in the wells were then observed and compared to the color chart. To obtain the number of motile sperm in the sample, the concentration obtained in row B, was subtracted from the concentration obtained in row A. To obtain sperm count, the concentration obtained from row B alone was used. For leukocyte count, the presence of blue color in row C corresponded to >1 million leukocytes/mL and the absence of color to ≦1 million/mL.

Study

The objective of this study was to evaluate the performance of a novel kit in the determination of sperm count, sperm motility and leukocyte count in semen, as compared to microscopic analysis. A total of 50 semen samples were obtained from 50 males presenting for infertility screening. Aliquots of the liquefied semen were scored for sperm count, sperm motility and leukocyte count in semen by microscopic analysis. Sperm concentrations ranged between 15 and 85 million/ml sperm motility between 10 and 90% and leukocyte count between 0.2 and 3 million/ml.

Sperm count, sperm fertility and leukocyte count in semen were determined using a multitest kit as follows: 50 µl of the liquefied semen was added to a 4×3, 12-well dot blot cartridge, 50 µl of 0.1% Triton X-100 in PBS and 50 µl of propidium iodide in PBS (1 mg/ml) was added to all four wells in row A, 50 µl of propidium iodide was also added to wells in row B. and 50 µl of TMB/$H_2O_2$ was added to wells in row C. All wells were rinsed with 50 µl distilled water using a multipipette. Rows A and B were used to obtain sperm count and the number of permeabilized sperm, respectively, and row C was used to determine leukocyte count in semen.

The color produced on the filter was then scanned in the transmittance mode using a densitometer. Correlation between the integration areas obtained for the colored dots by densitometric analysis and the values obtained by microscopic analysis was obtained by regression analysis. A significant correlation was found between sperm count and Triton X-100/propidium iodide-stained sperm (r=0.96); the number of spermatozoa stained with propidium iodide in the absence of 0.1% Triton X-100 treatment was highly correlated with the percent of immotile sperm in semen (r=0.95). Leukocyte count in semen by brightfield microscopy was also highly correlated with the densitometric values (r=0.97).

These results indicate that the multitest kit provides an objective and accurate means for the determination of sperm count, percent motility and leukocyte count in semen.

EXAMPLE 10

5-Way Semen Analysis Test Kit

Kit Components
1) (1) collection container (optional);
2) (1) multipipette;
3) (1) 20-well dot blot cartridge (e.g. 4"×3");
4) (1) container containing at least 5×50 µl of 0.1% Triton X-100 solution in phosphate buffered saline (PBS);
5) (1) container containing at least 10×50 µl of propidium iodide (1 mg/ml) in phosphate buffered saline (PBS);
6) (1) container containing at least 5×50 µl of tetramethylbenzidine $H_2O_2$ (TMB/$H_2O_2$) in dimethylformamide (Diatech Inc., Allston, Mass.) "TMB/$H_2O_2$ reagent";
7) (1) container containing at least 5×50 µl of protein A bound colloidal gold solution.
8) (1) container containing at least 5×50 µl of anti-SOD antibody bound gold colloidal solution;
9) (1) container containing at least 25×50 µl of d$H_2O$;
10) a color chart or densitometer; and
11) instructions for use.

Procedure

If semen was collected in the collection container, it was allowed to stand at room temperature for about 30 minutes in order for the semen to liquefy.

Using the multipipette, 50 µl of the liquefied semen was added to each well of the dot blot cartridge; 50 µl of 0.1% Triton X-100 solution in PBS and 50 µl of propidium iodide in PBS (1 mg/ml) was added to all five wells in row A; 50 µl of propidium iodide in PBS (1 mg/ml) was also added to all five wells in row B; 50 µl of tetramethylbenzidine $H_2O_2$ (TMB) in dimethylformamide was added to all five wells in row C; 50 µl of protein A bound colloidal gold solution was added to all five wells in row D; and 50 µl of anti-SOD antibody bound gold colloidal solution was added to all five wells in row E. 50 µl of d$H_2O$ was then added to all twenty five wells using a micropipette. Rows A and B were used to obtain sperm count and the number of permeabilized sperm (fertile sperm) respectively; row C was used to determine leukocyte count in semen; row D was used to determine sperm-bound antibodies; and row E was used to determine SOD immunoreactivity.

The color intensities in the wells were then observed and compared to the color chart. To obtain the number of motile sperm in the sample, the concentration obtained in row B, was subtracted from the concentration obtained in row A. To obtain sperm count, the concentration obtained from row B alone was used. For leukocyte count, the presence of blue color in row C corresponded to >1 million leukocytes/mL and the absence of color to ≦1 million/mL. An increasingly dark pink color in row D corresponds to a greater concentration of sperm bound antibodies and a very light pink color corresponds to no or very little sperm bound antibodies. Finally, the presence of a bright pink color in row E corresponds to high SOD immunoreactivity; the absence of color to low SOD and faint color to borderline SOD immunoreactivity.

EXAMPLE 11

Method for Determing Sperm Count Using Anti-Sperm Antibodies Conjugated to Detectable Particles (Plus (+) or Minus (-) Approach)

The ejaculate is collected in the collection tube (tube #1) containing 5 mg/mL of chymotrypsin in an isotonic solution. After about 3 to 5 minutes (at which time the semen should be liquefied) a drop (50 μl) (to determine male fertility) or 0.5 mL (to determine efficacy of male contraceptive) of the liquefied semen is added to another test tube (tube #2) containing a hypotonic solution. After a period of incubation of 5 minutes, a drop (about 50 μL) (to determine male fertility) or the total contents (to determine efficacy of male contraceptive) is transferred to a membrane provided with two windows: window #1 is used to apply the sample where after the sample is applied, the soluble sperm antigens react with anti-human sperm antibodies conjugated to gold or colored latex particles included in a reservoir in the membrane; window #2 has a horizontal colored line. As the sperm antigen/antibody/particle complex migrates through the membrane, a second anti-human sperm antibody bound in the vertical position to the membrane underlying window #2 (capture antibody) reacts with the sperm antigen/antibody/particle complex producing a colored vertical line when the sperm concentration in semen is above 50,000 spermatozoa/mL in which case a plus (+) sign appears. If the concentration of sperm in semen is below 50,000 spermatozoa/mL, a minus (−) sign appears.

EXAMPLE 12

Sperm Count Assay Using Anti-Sperm Antibodies Conjugated to Detectable Particles (Filter Approach)

Kit Components
1) (1) calibrated semen collection tube;
2) (1) squeeze bottle containing the chymotrypsin solution;
3) (1) test tube containing the isotonic or hypotonic solution;
4) (2) droppers;
5) (1) filter mounted on a liquid reservoir;
6) (1) squeeze bottle containing anti-sperm antibody-coated colored latex or gold particle solution;
7) instructions for use.

Procedure

Using the squeeze bottle, chymotrypsin solution (dextran-free) was added to the semen collection tube in a volume equal to the semen volume. The mixture was allowed to stand at room temperature for about 5 minutes in order for the semen to liquefy.

Using a dropper, one drop (to determine male fertility) or 0.5 ml (to determine efficacy of male contraceptive) of the semen/chymotrypsin mixture in the semen collection tube was added to another test tube (test tube #2) containing an isotonic solution (e.g. phosphate buffered saline or Earle's Medium) or a hypotonic solution (e.g. distilled water).

One drop (50 μL) (to determine male fertility) or 0.5 ml (to determine efficacy of male contraceptive) of test tube #2 was added to a filter (e.g. blocked nitrocellulose, 5 μm pore size or microfiber glass filter, 2.7 μm pore size) mounted on a liquid reservoir. Seminal plasma proteins, which were about 10–20 nm in size passed through the filter, while sperm cells which were about 1000 times bigger (50 μm in size) were retained.

One drop of anti-sperm antibody-coated colored particles (e.g. gold particles that have an intrinsic pink color; or a colored latex particle) was added onto the filter and the appearance of color on the filter indicated a potentially fertile sperm sample. By using this filter procedure, the antibody used to coat the latex particle did not have to be highly specific for the sperm cell (i.e. it could exhibit some cross-reactivity with seminal plasma proteins).

EXAMPLE 13

Sperm Count Assay Using Detectably Labeled Anti-Sperm Antibodies (Filter Approach with Preincubation of the Antibody and the Sperm Antigens)

Kit Components
1) (1) calibrated semen collection tube;
2) (1) squeeze bottle containing the chymotrypsin solution;
3) (1) test tube containing the isotonic or hypotonic solution;
4) (2) droppers;
5) (1) filter mounted on a liquid reservoir;
6) (1) squeeze bottle containing anti-sperm antibody-coated colored latex or gold particle solution;
7) instructions for use.

Procedure

Using the squeeze bottle, chymotrypsin solution (dextran-free) was added to the semen collection tube in a volume equal to the semen volume. The mixture was allowed to stand at room temperature for about 5 minutes in order for the semen to liquefy.

Using a dropper, one drop (about 50 μL) (to determine male fertility) or 0.5 mL (to determine efficacy of male contraceptive) of the semen/chymotrypsin mixture in the semen collection tube was added to another test tube (test tube #2) containing anti-sperm antibody-coated colored particles (e.g. gold particles that have an intrinsic pink color; or a colored latex particle) in an isotonic solution (e.g. phosphate buffered saline or Earle's Medium) or hypotonic solution (e.g. distilled water).

One drop (50 μL) (to determine male fertility) or 0.5 mL (to determine efficacy of male contraceptive) of the contents of test tube #2 was added to a filter (e.g. nitrocellulose, 5 μm pore size or microfiber glass filter, 2.7 μm pore size) mounted on a liquid reservoir. Seminal plasma proteins/color particle antibody/complex, which were about 10–20 nm in size passed through the filter, while sperm cells/colored particle antibody/complex which were about 1000 times bigger (50 μm in size) were retained. By using this filter procedure, the antibody used did not have to be highly specific for the sperm cell (i.e. it could show some cross-reactivity with seminal plasma proteins).

EXAMPLE 14

Sperm Count Assay Using Anti-Sperm Antibodies (Agglutination Approach)

Kit Components
1) (1) calibrated semen collection tube;
2) (1) squeeze bottle containing the chymotrypsin solution;
3) (1) test tube containing an isotonic or hypotonic solution and sperm-specific antibody-coated particles (uncolored or colored);
4) (2) droppers;
5) (1) slide having a color, which contrasts with the anti-sperm antibody-coated particles.
6) instructions for use.

Procedure

Using the squeeze bottle, chymotrypsin solution (dextran-free) was added to the semen collection tube (tube #1) in a volume equal to the semen volume. The mixture was allowed to stand at room temperature for about 5 minutes in order for the semen to liquefy.

Using a dropper, one drop (50 μL) (to determine male fertility) or 0.5 ml (to determine the efficacy of a male contraceptive) of the semen/chymotrypsin mixture was added to another test tube (test tube #2) containing an isotonic solution (e.g. phosphate buffered saline or Earle's Medium) or hypotonic solution (e.g. distilled water) and sperm-specific antibody-coated particles (uncolored or colored).

One drop of test tube #2 was deposited on a slide, which was of a color that contrasted with the sperm specific antibody coated latex particles, so that agglutination, indicating the potential presence of fertile sperm could be discerned on the slide. The absence of agglutination when determining male fertility, was indicative of less than about 20 million spermatozoa/mL and the presence of agglutination was indicative of greater than about 20 million spermatozoa/mL.

EXAMPLE 15

Sperm Count Assay (Non-Immunoreactive/Filter Approach)
Kit Components
1) (1) calibrated semen collection tube;
2) (1) squeeze bottle containing the chymotrypsin solution;
3) (1) test tube containing the isotonic or hypotonic solution;
4) (2) droppers;
5) (1) filter mounted on a liquid reservoir;
6) (1) squeeze bottle containing colored reagents that react non-specifically with sperm cell components, e.g., pink-colored gold particles (reacts with proteins) or red-colored rhodamine (reacts with lipids).
7) instructions for use.
Procedure Using the squeeze bottle, chymotrypsin solution (dextran-free) was added to the semen collection tube (tube #1) in a volume equal to the semen volume. The mixture was allowed to stand at room temperature for about 5 minutes in order for the semen to liquefy.

Using a dropper, one drop (50 $\mu$L) (to determine male fertility) or 0.5 ml (to determine efficacy of a male contraceptive) of the liquefied semen was added to another test tube (tube #2) containing gold particles (that have an intrinsic pink color) in a hypotonic or isotonic solution. One drop (to determine male fertility) or 0.5 $\mu$L (to determine efficacy of a male contraceptive) of the contents of tube #2 was added onto the filter (nitrocellulose with 5 $\mu$m pore size or microfiber glass filter with a pore size of 2.7 $\mu$m). Gold particles have an intrinsic pink color and high affinity for biomolecules (e.g. proteins or lipids) and therefore can bind to both spermatozoa and seminal plasma proteins. By using this filter procedure, the unbound gold particles and the gold particles bound to seminal plasma proteins went through the filter into the reservoir while sperm cells with bound gold particles were retained on the filter indicating a pink color. The presence of a pink color when male fertility was being evaluated, was indicative of the presence of greater than about 20 million spermatozoa/mL; and greater than about 100,000 spermatozoa/mL when the efficacy of a male contraceptive was being evaluated.

EXAMPLE 16

Assay for Identifying Sperm Samples with High Fertility Potential (Antibody Approach)
Kit Components
1) (1) calibrated semen collection tube containing 5 mg/mL, of chymotrypsin in an isotonic solution;
2) (1) tube containing anti-glutathione peroxidase (GPx) antibodies bound to yellow colored particles and anti-superoxide dismutase (SOD) antibodies bound to blue colored particles in a hypotonic or isotonic solution;
3) (1) dropper;
4) (1) porous filter mounted on a liquid reservoir;
5) instructions for use.
Procedure The ejaculate was collected in the collection tube (tube #1) containing 5 mg/ml of chymotrypsin in an isotonic solution. After about 3 to 5 minutes (at which time the semen should have been liquefied) a drop (about 50 $\mu$L) of the liquefied semen was added to a test tube (tube #2) containing anti-glutathione peroxidase (GPx) antibodies bound to yellow colored particles and anti-superoxide dismutase (SOD) antibodies bound to blue colored particles in a hypotonic or isotonic solution. The mixture was incubated for up to about 10 minutes to allow the sperm antigens exposed after the hypotonic treatment to react with the antibodies.

Following incubation, the contents of test tube #2 was transferred to a filter membrane, so that sperm/colored particle/antibody complex was retained and unbound, colored particle/antibody passed through the filter into a reservoir.

If the filter appeared green, the SOD/GPx ratio was about 1:1 and the sample had borderline pregnancy potential; if the filter appeared bluish, high SOD content was indicated and the sample had high pregnancy potential; and if the filter appeared yellowish, low SOD content was indicated and the sample had low pregnancy potential.

EXAMPLE 17

Assay for Determining Sperm Count (non-antibody approach)
Kit Components
1) (1) calibrated semen collection tube;
2) (1) squeeze bottle containing the liquefying enzyme (e.g. chymotrypsin or pronase at 5 mg/ml.) (squeeze bottle #1);
3) (1) squeeze bottle (with a removable top) containing 150 $\mu$L of an isotonic or hypotonic solution (squeeze bottle #2);
4) (1) squeeze bottle containing a 0.5 mg/mL solution of Rhodamine-123 (Molecular Probes, Inc. Eugene, Oreg.) in distilled water (squeeze bottle #3);
5) (1) dropper;
6) (1) porous filter mounted on a liquid reservoir;
7) instructions for use.
Procedure Using the squeeze bottle provided (squeeze bottle #1), two drops (per milliliter of semen) of a solution of pronase solution (5 mg/mL) (Sigma Chemical Corp., St. Louis, Mo.) in Earle's medium was added to the ejaculate in the collection tube. The mixture was allowed to stand at room temperature for about 5 minutes in order for the semen to liquefy.

Using a dropper, one drop (to determine male fertility) or four drops (to determine efficacy of a male contraceptive) of the liquefied semen was added to another squeeze bottle (squeeze bottle #2) which had the top removed and contained 150 $\mu$L (to determine male fertility) or 250 $\mu$L (to determine efficacy of a male contraceptive) of a hypotonic solution. Then, one drop (to determine male fertility) or 4 drops (to determine efficacy of a male contraceptive) of the Rhodamine-123 (Molecular Probes, Inc. Eugene, Oreg.) solution in squeeze bottle #3 was added to squeeze bottle #2 and the top placed back on. The contents were then mixed by tapping with a finger.

Two drops (to determine male fertility) or the total content of squeeze bottle #2 was added to a porous filter (about 2.7 $\mu$m pore size) mounted on a liquid reservoir and the color visualized. The absence of color was indicative of a concentration of less than about 20 million spermatozoa/mL; faint color was indicative of greater than about 20 million spermatozoa/mL and less than about 40 million spermatozoa/mL; and the presence of color was indicative of greater than about 40 million spermatozoa/mL.

EXAMPLE 18

Test Kit for the Determination of Sperm Chromatin Decondensation

This assay is particularly useful to monitor sperm fertility/motility at a physician's office, andrology lab, veterinary office or animal farm. In addition the test can be used to determine the fertility of semen samples obtained from farm animals, e.g., horse, bovine, porcine. Further the test can be used in research as a semiquantitative assay of sperm viability/motility.

Kit Components
1) (1) collection container containing about 10 mg of lyophilized chymotrypsin (optional);
2) (3) droppers;
3) (1) filter module [e.g. Progene Corporation, cat # 000012];
4) (1) container containing at least one drop (50 μl) of dithiothreitol (DTT) in PBS;
5) (1) container containing at least two drops (100 μl) of acridine orange (2 mg/ml) in PBS; and
6) instructions for use.

Procedure

Semen was collected in the collection container containing chymotrypsin. The mixture was allowed to stand at room temperature for about 15 minutes in order for the semen to liquefy (optional step).

Using a first dropper, one drop (50 μl) of the liquefied semen (or optionally washed sperm) was added to a first well (well #1) of the filter module and two drops (100 μl) of semen or washed sperm was added to a second well (well #2). After the liquid had drained, one drop of dithiothreitol (DTT) (Sigma) in PBS was added to well #1. After the liquid had drained, one drop of acridine orange (Molecular Probes) (2 mg/ml) in PBS was added to both well #1 and well #2.

The color intensity observed in each well was then compared. The color intensity in well #1 is proportional to the number of sperm in the sample. The color intensity in well #2 is proportional to the number of sperm with decondensed chromatin. If the color intensity in test well #2 is equal to that in well #1, 50% of the sperm have their nuclear chromatin decondensed, if the color intensity in well #2 is lower than that in well #1, less than 50% of the sperm have their chromatin decondensed; and if the color intensity in well #2 is higher than that in well #1, more than 50% of the sperm have their chromatin decondensed. The color produced on the filter ranges from a light to a deep yellow.

Those skilled in the art will recognize, or be able to ascertain using no more than routine experimentation, many equivalents to the specific embodiments of the invention described herein. Such equivalents are intended to be encompassed by the following claims.

I claim:

1. A home test kit for home use for screening male factor fertility, comprising:
   a collection container for collecting a sperm containing sample, wherein the collection container contains a liquefying reagent for liquefying the sample;
   a thiazine blue reagent for applying to a filter in conjunction with at least a portion of the sample to complex with and color sperm in the sample;
   a filter module containing a filter to which at least a portion of the sample and the thiazine blue reagent are applied, wherein said filter has a porosity that retains sperm complexed with the thiazine blue reagent and permits uncomplexed thiazine blue reagent to pass and wherein said filter exhibits a characteristic coloring due to coloring of the sperm by the thiazine blue reagent if the sample is fertile.

2. The home test kit of claim 1 wherein the liquefying reagent is chymotrypsin.

3. The home test kit of claim 1 further comprising a wash solution for adding to the filter to ensure that the uncomplexed thiazine blue reagent passes through the filter.

4. The home test kit of claim 1 further comprising a condom for collecting the sample prior to collection by the collection container.

5. The home test kit of claim 1 wherein the thiazine blue reagent has a thiazine blue concentration such that the thiazine blue reagent colors the sperm so that the filter exhibits the characteristic coloring when at least 20 million spermatozoa/ml are present in the portion of the sample that was applied to the filter.

6. The home test kit of claim 1 wherein the thiazine blue reagent has a thiazine blue concentration such that the thiazine blue reagent colors the sperm so that the filter exhibits the characteristic coloring when at least 0.1 million spermatozoa/ml are present in the portion of the sample that was applied to the filter.

7. The home test kit of claim 1 wherein the liquefying reagent is dried.

8. The home test kit of claim 1 wherein the filter is a microfiber glass filter.

9. The home test kit of claim 1 wherein the filter has a pore size in the range of about 2.7 μm to 5.0 μm.

10. A method of determining a fertility potential of a sample containing sperm, comprising the steps of:
    adding a sample containing sperm to a collection container, wherein said collection container contains a liquefying reagent;
    waiting for the sample to liquefy;
    adding a portion of the liquefied sample to a filter;
    adding a thiazine blue reagent to complex with and color sperm in the portion of the sample that is added to the filter, wherein the filter has a porosity that retains sperm complexed with the thiazine blue reagent and passes uncomplexed thiazine blue reagent; and
    determining the fertility potential of the sample by detecting the presence or absence of characteristic coloring due to coloring of the sperm by the thiazine blue reagent.

11. The method of claim 10 wherein the liquefying reagent is chymotrypsin.

12. The method of claim 10 further comprising the step of adding a wash solution to the filter to ensure that the uncomplexed thiazine blue reagent passes through the filter before the determining step.

13. The method of claim 10 further comprising the steps of:
    initially collecting the sample in a condom;
    transferring the sample from the condom to the collection container.

14. The method of claim 10 wherein the thiazine blue reagent has a thiazine blue concentration such that the reagent colors the sperm so that the filter exhibits the characteristic coloring when at least 20 million spermatozoa/ml are present in the portion of the sample that was added to the filter.

15. The method of claim 10 wherein the thiazine blue reagent has a thiazine blue concentration such that the thiazine blue reagent colors the sperm so that the filter exhibits the characteristic coloring when at least 0.1 million spermnatozoa/ml are present in the portion of the sample that was added to the filter.

16. The method of claim 10 wherein the liquefying reagent is dried.

* * * * *